US00PP16797P3

(12) United States Plant Patent
Saville

(10) Patent No.: US PP16,797 P3
(45) Date of Patent: Jul. 11, 2006

(54) MINIATURE ROSE PLANT NAMED 'SAVADIANA'

(50) Latin Name: *Rosa hybrida minima*
Varietal Denomination: SAVadiana

(75) Inventor: John Saville, Newburport, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 10/303,485

(22) Filed: Nov. 25, 2002

(65) Prior Publication Data

US 2005/0246804 P1 Nov. 3, 2005

(51) Int. Cl.
*A01H 5/00* (2006.01)

(52) U.S. Cl. ..... Plt./118
(58) Field of Classification Search ..... Plt./118
See application file for complete search history.

(56) References Cited

U.S. PATENT DOCUMENTS

| | | | | | |
|---|---|---|---|---|---|
| PP6,859 | P | * | 6/1989 | Laver | Plt./119 |
| PP7,941 | P | * | 8/1992 | Warriner | Plt./118 |
| PP8,453 | P | * | 11/1993 | Moore | Plt./118 |
| PP9,506 | P | * | 4/1996 | Saville | Plt./118 |
| PP11,136 | P | * | 11/1999 | Kordes | Plt./118 |
| PP11,810 | P2 | * | 3/2001 | Saville | Plt./125 |

* cited by examiner

*Primary Examiner*—Kent Bell
*Assistant Examiner*—W. C. Haas

(57) ABSTRACT

'SAVadiana' is a new and distinct variety of miniature rose plant primarily identified by it's continuous display of small deep yellow buds and flowers on a well branched and compact plant. The flowers last well when cut and can be easily dried, maintaining their deep yellow coloring. SAVadiana, having very good disease resistance, is easy to grow outdoors as a garden perennial, low growing hedge, specimen plant or in containers, or in the greenhouse.

1 Drawing Sheet

Genus and species: *Rosa hybrida 'minima'*.
Varietal denomination: 'SAVadiana'.

CROSS REFERENCE

This new invention bares resemblance to two miniature rose plants from the same breeding program with which it shares the seed parent of 'MORpoly' (U.S. Plant Pat. No. 8,453). They are 'SAVyk' (U.S. Plant patent application Ser. No. 09/731,482, filing date of Mar. 20, 2001, examiner Howard J. Locker, abandoned) and 'SAVanade' (U.S. Plant Pat. No. 11,810) both which have similar non-fading, deep yellow blooms. The most notable difference between these three plants is that this new invention has a smaller bloom size and a more compact plant habit than the other two. It is also more densely branched and more vigorous than 'SAVyk' and is considerably shorter than 'SAVanade'.

RIGHTS TO THE INVENTION

Be it known that John M. Saville of Newburyport in the county of Essex in the state of Massachusetts claims invention of new and useful improvements in ROSE PLANT/var. 'SAVadiana' and following is a clear and exact description of the same.

BACKGROUND OF THE INVENTION

This present invention relates to a new and distinct variety of hardy, bush type plant of the miniature rose class. This new variety was created in a greenhouse in Rowley, Mass. by crossing the following two rose plants:

The seed parent is 'MORpoly' (U.S. Plant Pat. No. 8,453)

The pollen parent is 'LAVjun' (U.S. Plant Pat. No. 6,859)

The primary objective of this hybridization was to create a new floriferous, deep yellow miniature rose with hybrid tea form.

The similarities between this new invention and its seed parent, 'MORpoly' are vigor, disease resistance and very little fade of the yellow flowers as they age. The differences between these two are that the color of the flowers of this new invention are a darker yellow and most of the flowers are borne singly in contrast to the clusters on 'MORpoly'. The new invention also has a more compact plant habit.

The traits acquired by this new invention from its pollen parent, 'LAVjun', are its hybrid tea flower form and those flowers being borne mostly singly. The noticeable differences between these two are the new invention is more vigorous, more well branched and with thinner and smaller petals resulting in somewhat smaller open blooms.

Asexual reproduction by cuttings of this new variety in Rowley, Mass. shows that all distinguishing characteristics of this rose continually come true to form.

SUMMARY OF THE INVENTION

The present invention relates to a new and distinct variety of hardy dwarf bush type rose plant of the miniature class; the variety being primarily characterized—as to novelty—by its small deep yellow buds and flowers of hybrid tea form on a well branched, vigorous and compact plant. The variety is further characterized by:

A plant that flowers continuously all season

Flowers that last well when cut

Flowers that hold their dark yellow color when dried

Little fragrance

Excellent resistance to blackspot

Good tolerance to both cold and heat

A plant which grows and blooms satisfactorily both in the greenhouse and outdoors: as a garden perennial, specimen plant or in containers.

BRIEF DESCRIPTION OF THE DRAWING

The accompanying color photograph taken in November shows specimens of the buds, flowers and foliage of this new variety in different stages of development as grown and observed under plastic in Essex County, Massachusetts. (Spotting, noted only on the petals of the full blown bloom, is damage from a spray being used in the greenhouse to treat other adjacent plants for diseases. Only petals that are about to drop were affected.)

BOTANICAL DESCRIPTION OF THE PLANT

Following is a detailed description in outline form pertaining specifically to this new and distinct variety of miniature rose plant as observed on 4 and 5 year old plants grown in containers, indoors under plastic, in Essex County, Massachusetts. All major color plate identifications made are referring to The Royal Horticulture Society Chart except where common terms of color definition are employed.

Genus/species: *Rosa hybrida 'minima'*.
Commercial class: Miniature Rose.
Varietal denomination: 'SAVadiana'.

*Size.*—Medium, 7/16 to 8/16 inch diameter at the widest point and about 5/8 inch long just before the sepals divide.

*Form.*—Ovate.

*Color.*—When sepals first divide — deep yellow near 14B.

*Sepals.*—Surface texture — outside, glabrous, inner surface, pubescent. Color — outer surface near 144A and with central, weak anthocyanin coloring of a greyed-red, near 179C; the inner surface is a light yellow-green appearing near 151C and with a darker green, near 138C, along the margins. Edge — fine, evenly serrated margins with anthocyanin coloration. Width — about 9/32 inch. Length — about 1 1/8 inches. Characteristics — lanceolate; extending beyond the tip of the bud by about 1/2 inch; margins of the two innermost sepals are ciliate; the margins of the three outer sepals are ciliate and with stipitate glands and occasionally one thin, acuminate, foliaceous appendage on one or both margins; rolling almost back to the stem as the flowers open; remaining attached to the receptacle; and the peduncle and the receptacle with the sepals still attached dry and drop together.

*Peduncle.*—Length — averaging 1 1/16 to 1 7/16 inches with a direct correlation to the length of the flowering stem. Aspect — straight. Strength — erect, strong. Texture — glabrous, with stipitate glands having anthocyanin coloring and varying from very few to a small amount. Color — light yellow-green, between 144B and 145C.

*Receptacle.*—5/16" diameter. Color — near 144B. Texture — glabrous.

Bloom:

*Size.*—When fully expanded — 1 3/4 to 1 7/8 inches wide and 3/8 to 1/2 inch high, measured from the receptacle.

*Form.*—High centered at first and when full open having a flattened convex upper profile, and a flat lower profile and with petals remaining reflexed.

*Petalage.*—Usually 20.

*Petaloids.*—3 or 4, varying in size from 1/8 to 1/2 inch wide and 1/2 to 5/8 inch long, but similar in shape and coloration to the petals, being a deep lemon yellow, between 15A and 15B and the reverse also a deep lemon yellow, near 14B; during the first few days, and as the bloom ages they lighten only a little, first to between 13B and 13C with the reverse still being near 14B and finally to near 12C on the upper surface and near 10A on the reverse.

*Fragrance.*—Very slight.

*Persistence.*—Blooms last 6 to 8 days on the plant: petals then drop off cleanly in about 2 days.

*Lasting quality as a cut flower.*—4 to 7 days.

Petals:

*Texture.*—Glabrous, medium thickness.

*Appearance.*—Inside — velvety, outside —satiny.

*Form.*—Broad fan shaped with the apex being one single serration at the outer center of the margin, reflexing back from either side of the apex to give an overall appearance of being deltoid.

*Size.*—About 13/16 inch at the widest part of the outer petals and about 7/8 inch long.

*Arrangement.*—Arranged shingle-like.

*Color.*—During the first few days, inner and outer petals are a deep lemon yellow, between 15A and 15B and the reverse also a deep lemon yellow, near 14B; as the bloom ages it lightens only a little, first to between 13B and 13C with the reverse still being near 14B and finally to near 12C on the upper surface and near 10A on the reverse, drying at this color and then dropping from their attachment to the receptacle.

*General tonality.*—Deep yellow.

REPRODUCTIVE ORGANS

Stamens, filaments and anthers:

*Arrangement.*—Regularly arranged around styles.

*Quantity.*—Around 80.

*Filaments.*—Length — varying from 1/8 inch to 5/16 inch general color — near 23A.

*Anthers.*—Color — between 153B and 153C.

Pollen:

*Color.*—near 14D

*Quantity.*—Very small amount.

Pistils, styles and stigmas:

*Quantity.*—Less than 20.

*Styles.*—From 2/16 to 3/16 inch. Color — near 144C.

*Stigmas.*—Color — near 144D.

Hips:

*Shape.*—apple shaped.

*Size.*—About 3/4" diameter.

*Surface texture.*—Glabrous.

*Color.*—Near 169B and 169C.

*Seeds.*—Occasionally seeds partially protrude from the top of the hip. Color — pale yellow with just a hint of green.

PLANT

Habit: Upright, bushy and compact.

Growth: Vigorous and uniformly branched, maturing at a height of 16 to 22 inches and 12 to 14 inches wide.

Length of flowering stem: Averaging 4 to 4½ inches when borne singly.

Length of internodes: Usually 1 inch between nodes on laterals.

Foliage: Pinnately compound with 3 to 5 leaflets and occasionally 7 leaflets.

*Size of mature leaf.*—4 to 4½ inches from stem to tip when measured along the rachis.

*Quantity.*—Abundant such that there are no stems or laterals visible, being completely clothed with foliage.

*Leaflets.*—On the 5 leaflet leaves the basil leaflets are often not attached directly opposite each other and may be off by as much as ⅛ inch or as little as 1/64 inch. On a 7 leaflet leaf, the third and fourth sets of leaflets are often not opposite, with basil leaflets having the largest discrepancy and the third set of leaflets usually not being separated by more than 1/16 inch. Non-opposing basil leaflets are usually noticeably different in size. Size — mature terminal leaflet — averaging 1⅝ inches from base to tip but may be 2 inches in length, and being from ⅝ to 1 inch wide. Shape — oval with acute apex and ovate base. Edge — fine, even serration, with glands and stipitate glands at tip of each serrate with those glands that are stipitate usually being only on the serrate near the base of the leaflet. Color — new foliage — anthocyanin coloring present, upper surface, a dark olive green near 137C flushed very lightly with 183B and the very edge of the margin being near 183B and the reverse being near 146C and flushed very lightly with near 183B; older foliage — anthocyanin coloring absent, upper surface is a very dark green, between 147A and 139A, and the reverse being near 147B. Texture — both surfaces are glabrous; upper surface is smooth, reverse is leathery. Appearance — both surfaces matte; upper surface, veins slightly recessed; under surface, only the mid vein protruding slightly and the veins being a light yellow-green, near 145A. Petiole/rachis — color — new growth — upper surface is a flushed greyed-purple, near 183B; under surface is near 146B; old growth — anthocyanin coloring absent, upper surface is near 137C and the under surface is near 144A. Texture of the petiole/rachis — both surfaces are glabrous, the upper side is shallowly grooved with many stipitate glands along both ridges of the groove; under surface has a rare stipitate gland or prickles and occasionally having 1 to 3 very prickles which are near 174D in color.

*Petiolule.*—On the basal leaflets about 3/32 inch, for the remaining leaflets adjacent to the rachis about 1/32 inch. Color — upper surface is the same as that of the petiole, the under surface is lighter, near 145A.

*Stipules.*—Paired at the point of attachment of the petioles; elongate where attached to petiole then angling out at an angle of less than 45 degrees to an acuminate tip, on mature leaf averaging ½ inch attached and ¼ inch angled outward; margins are entire, tightly reflexed and lined with stipitate glands. Color: both surfaces are near 137B with the upper surface being semiglossy and the under surface being matte.

Resistance: Excellent resistance to black spot, good resistance to both powdery and downy mildew and to insects, no rust observed.

Wood:

*New Wood.*—Texture — smooth. Appearance — there are simple, microscopic hairs which decrease in quantity from the base toward the tip of each stem; as many as 40 or more per inch toward the base, graduating to none within 2 or more inches of the tip. Color — near 144A and flushed very lightly with near 185.

*Old wood.*—Texture — smooth. Appearance — no more than 3 simple, microscopic hairs per inch of stem, often none. Color — near 165A.

Thorns: Quantity on main stalks — few, usually 0 to 2 per inch and on laterals ordinary, ranging from 3 to 5 per stem inch.

*Form.*—A flat base tapering to a fine point, straight and angled slightly down, being ¼ to 3/16 inch in length.

*Color.*—When young — near 184D and somewhat translucent, when old — near 165A.

*Prickles.*—Occasionally 1 to 3 prickles on underside of the rachis only.

Winter hardiness: Tested hardy in zones 4 through 9 with ample winter protection recommended zones 5 and colder.

Heat tolerance: Plants held up very well under testing in American Horticultural Society heat zones 9 through 1.

It is claimed:

1. I claim a new, distinct variety of hardy miniature rose plant substantially as illustrated and described which, in season, continuously bears numerous, small, vivid yellow buds and flowers of hybrid tea form on a low growing, well branched and compact bush with very good disease resistance.

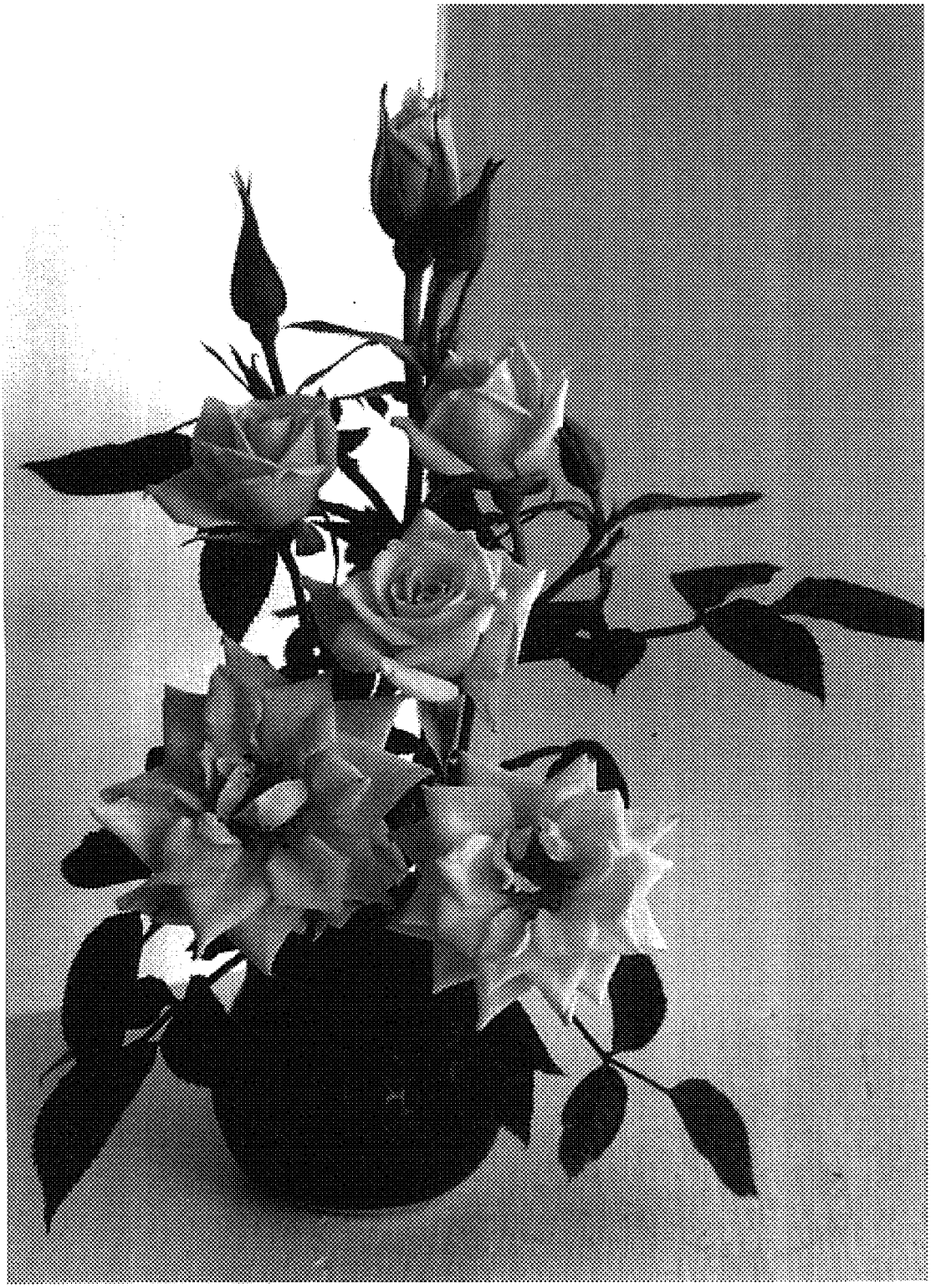

* * * * *